(12) United States Patent
Luscher

(10) Patent No.: US 8,665,439 B2
(45) Date of Patent: Mar. 4, 2014

(54) METHOD AND APPARATUS FOR LIMITING EFFECTS OF REFRACTION IN CYTOMETRY

(75) Inventor: Mark Luscher, Toronto (CA)

(73) Assignee: Microbix Biosystems, Inc., Mississauga (CA)

( * ) Notice: Subject to any disclaimer, the term of this patent is extended or adjusted under 35 U.S.C. 154(b) by 476 days.

(21) Appl. No.: 12/495,437

(22) Filed: Jun. 30, 2009

(65) Prior Publication Data

US 2010/0328664 A1    Dec. 30, 2010

(51) Int. Cl.
*G01N 21/25*      (2006.01)
(52) U.S. Cl.
USPC ........................................................ 356/417
(58) Field of Classification Search
USPC ...................................... 356/417; 250/456.1
See application file for complete search history.

(56) References Cited

U.S. PATENT DOCUMENTS

| | | | |
|---|---|---|---|
| 2,656,508 A | 10/1953 | Coulter | |
| 3,380,584 A | 4/1968 | Fulwyler | |
| 3,497,690 A | 2/1970 | Wheeless, Jr. et al. | |
| 3,529,896 A * | 9/1970 | Padawer | 356/410 |
| 3,657,537 A | 4/1972 | Wheeless, Jr. et al. | |
| 3,710,933 A | 1/1973 | Fulwyler et al. | |
| 3,954,341 A * | 5/1976 | Uffenheimer | 356/410 |
| 4,021,117 A | 5/1977 | Gohde et al. | |
| 4,188,542 A | 2/1980 | Hogg et al. | |
| 4,284,355 A * | 8/1981 | Hansen et al. | 250/461.2 |
| 4,395,397 A | 7/1983 | Shapiro | |
| 4,629,687 A | 12/1986 | Schindler et al. | |
| 4,998,022 A * | 3/1991 | Tregay | 356/136 |
| 5,135,759 A | 8/1992 | Johnson | |
| 5,153,679 A * | 10/1992 | Gilby | 356/328 |
| 5,184,192 A * | 2/1993 | Gilby et al. | 356/246 |
| 5,406,421 A | 4/1995 | Kashima et al. | |
| 5,495,105 A | 2/1996 | Nishimura et al. | |
| 5,544,182 A | 8/1996 | Nagaishi et al. | |
| 5,608,517 A * | 3/1997 | Munk | 356/328 |
| 5,658,892 A | 8/1997 | Flotte et al. | |

(Continued)

FOREIGN PATENT DOCUMENTS

| | | |
|---|---|---|
| DE | 1815352 A1 | 1/1971 |
| WO | WO-98/34094 A1 | 8/1998 |

(Continued)

OTHER PUBLICATIONS

International Search Report and Written Opinion for Application No. PCT/IB2009/006412, dated Mar. 26, 2010.

(Continued)

*Primary Examiner* — Kara E Geisel
(74) *Attorney, Agent, or Firm* — Marshall, Gerstein & Borun LLP

(57) ABSTRACT

A method and apparatus for performing cell cytometry mitigate or eliminate the effects of refraction that result from interfaces between materials having different refractive indices. Solid materials, such as the walls of a flow path, which materials are disposed between a nominal focal point and an objective lens, are formed of a material having a refractive index between 1.30 and 1.40 inclusive. The refractive index of a liquid material, such as an immersion fluid or a fluid carrying, suspending, or bathing an analyte, may be adjusted to have a refractive index closer to that of surrounding solid materials and, in particular, within 0.02 of the refractive index of the surrounding solid materials.

28 Claims, 12 Drawing Sheets

(56) References Cited

U.S. PATENT DOCUMENTS

| | | | |
|---|---|---|---|
| 5,739,902 A | 4/1998 | Gjelsnes et al. | |
| 6,010,647 A | 1/2000 | Nomura et al. | |
| 6,143,535 A | 11/2000 | Palsson | |
| 6,245,508 B1* | 6/2001 | Heller et al. | 356/317 |
| 6,320,705 B1 | 11/2001 | Dube' | |
| 6,388,746 B1* | 5/2002 | Eriksson et al. | 356/318 |
| 6,473,238 B1 | 10/2002 | Daniell | |
| 6,534,308 B1 | 3/2003 | Palsson et al. | |
| 6,594,009 B2 | 7/2003 | Saccomanno | |
| 6,797,139 B2 | 9/2004 | Bahatt et al. | |
| 6,816,182 B2 | 11/2004 | Kubota et al. | |
| 7,106,528 B2 | 9/2006 | Ohmori et al. | |
| 7,118,676 B2 | 10/2006 | Mueth et al. | |
| 7,193,775 B2 | 3/2007 | Olszak et al. | |
| 7,355,696 B2 | 4/2008 | Mueth et al. | |
| 7,586,604 B2 | 9/2009 | Sharpe et al. | |
| 2002/0125230 A1 | 9/2002 | Haight et al. | |
| 2003/0087860 A1 | 5/2003 | Mileham et al. | |
| 2003/0137661 A1 | 7/2003 | Ortyn et al. | |
| 2003/0180955 A1* | 9/2003 | Ozasa et al. | 436/10 |
| 2004/0012676 A1 | 1/2004 | Weiner et al. | |
| 2004/0189977 A1 | 9/2004 | Nagai et al. | |
| 2005/0019842 A1 | 1/2005 | Prober et al. | |
| 2005/0112541 A1 | 5/2005 | Durack et al. | |
| 2005/0194546 A1 | 9/2005 | Saccomanno | |
| 2006/0170912 A1 | 8/2006 | Mueth et al. | |
| 2006/0192940 A1 | 8/2006 | Phi-Wilson | |
| 2006/0203226 A1 | 9/2006 | Roche et al. | |
| 2006/0263829 A1 | 11/2006 | Evans et al. | |
| 2007/0047868 A1 | 3/2007 | Beaulieu et al. | |
| 2007/0117086 A1 | 5/2007 | Evans et al. | |
| 2007/0215817 A1* | 9/2007 | Shirai et al. | 250/458.1 |
| 2008/0094627 A1* | 4/2008 | Oldham et al. | 356/344 |
| 2008/0144037 A1 | 6/2008 | Mueth et al. | |
| 2008/0213915 A1 | 9/2008 | Durack et al. | |
| 2010/0284016 A1* | 11/2010 | Teitell et al. | 356/451 |
| 2011/0089315 A1 | 4/2011 | Walt et al. | |
| 2011/0165025 A1* | 7/2011 | Gransee et al. | 422/82.05 |

FOREIGN PATENT DOCUMENTS

| | | |
|---|---|---|
| WO | WO-99/05504 A2 | 2/1999 |
| WO | WO-01/29538 A1 | 4/2001 |
| WO | WO-02/059273 A2 | 8/2002 |
| WO | WO-2004/088283 A2 | 10/2004 |
| WO | WO-2005/075629 A1 | 8/2005 |
| WO | WO-2008/128630 A1 | 10/2008 |

OTHER PUBLICATIONS

Asbury, et al., "Polarization of Scatter and Fluorescence Signals in Flow Cytometry," Cytometry vol. 40 pp. 88-101 (2000).

Fouque, et al., "Multiple wavelength fluorescence enhancement on glass substrates for biochip and cell analyses," Biosensors an Bioelectronics vol. 20 pp. 2335-2340 (2005).

Kummrow, et al., "Microfluidic structures for flow cytometric analysis of hydrodynamically focussed blood cells fabricated by ultraprecision micromachining," The Royal Society of Chemistry vol. 9 pp. 972-981(1999).

Seitzinger, et al., "Ray tracing analysis of the image quality of a high collection efficiency mirror system," Applied Optics vol. 29, No. 28 pp. 4255-4258 (1990).

Takahahi, et al., "Further advancement of wide-angle EUSO telescope with holographic and Fresnel lenses," 29th International Cosmic Ray Conference Pune 8, pp. 355-358 (2005).

Garner, et al., "Quantification of the X- and Y-Chromosome-Bearing Spermatozoa of Domestic Animals by Flow Cytometry," Biology of Reproduction 28, pp. 312-321 (1983).

Kawano, et al., "Ultrafast dynamics in a live cell irradiated by femtosecond laser pulses," Biophotonics 2007: Optics in Life Science, edited by Jürgen Popp, Gert von Bally, Proc. of SPIE-OSA Biomedical Optics, SPIE vol. 6633, pp. 66330J-1-66330J-9(2007).

Pitsillides, et al., "Selective Cell Targeting with Light-Absorbing Microparticles and Nanoparticles," Biophysical Journal, vol. 84, pp. 4023-4032 (2003).

Hung, et al., "Fluorinated Plastics, Amorphous," Concise Polymer Materials Encyclopedia, pp. 499-501 (1998).

Herweijer, et al., "High-Speed Photodamage Cell Selection Using Bromodeoxyuridine/Hoechst 33342 Photosensitized Cell Killing," Cytometry vol. 9, pp. 143-149 (1988).

Pinkel, et al., "High Resolution DNA Content Measurements of Mammalian Sperm," Cytometry vol. 3, No. 1, pp. 1-9 (1982).

Kerker, et al., "An Optical Model for Fluorescence of Mammalian Sperm in Flow Cytometry," Cytometry vol. 1, No. 2, pp. 161-167 (1980).

Martin, et al., "Photodamage, a Basis for Super High Speed Cell Selection," Cytometry vol. 2, p. 2 (Abstract) (1981).

Severin, et al., "A New Flow Chamber and Processing Electronics for Combined Laser and Mercury Arc Illumination in an Impulscytophotometer Flow Cytometer," Cytometry, vol. 3, No. 4, pp. 308-310 (1983).

Bakker Schut, et al., "A New Principle of Cell Sorting by Using Selective Electroporation in a Modified Flow Cytometer," Cytometry, vol. 11, pp. 659-666 (1990).

Keij, et al., "Coincidence in High-Speed Flow Cytometry: Models and Measurements," Cytometry, vol. 12, pp. 398-404 (1991).

Keij, et al., "High-Speed Photodamage Cell Selection Using a Frequency-Doubled Argon Ion Laser," Cytometry, vol. 19, pp. 209-216 (1995).

Evenson, et al., "Comparative Sperm Chromatin Structure Assay Measurements on Epiillumination and Orthogonal Axes Flow Cytometers," Cytometry, vol. 19, pp. 295-303 (1995).

Sharpe, et al., "Radially Symmetric Excitation and Collection Optics for Flow Cytometric Sorting of Aspherical Cells," Cytometry, vol. 29, pp. 363-370 (1997).

Koller, et al., "High-Throughput Laser-Mediated In Situ Cell Purification with High Purity and Yield," Cytometry Part A, vol. 61A, pp. 153-161 (2004).

Cytop®, "Amorphous Fluorocarbon Polymer," (undated) Available at http://www.belexinternational.com/Cytopflyer.pdf.

Gledhill, "Cytometry of Mammalian Sperm," Gamete Research, vol. 12, pp. 423-438 (1985).

Egner, et al., "Aberrations in Confocal and Multi-Photon Fluorescence Microscopy Induced by Refractive Index Mismatch," Handbook of Biological Confocal Microscopy, third edition, (2006).

Van Dilla, et al., "Measurement of Mammalian Sperm Deoxyribonucleic Acid by Flow Cytometry," The Journal of Histochemistry and Cytochemistry, vol. 25, No. 7, pp. 763-773 (1977).

Otto, et al., "Flow Cytometry of Human Spermatozoa," Histochemistry 62, pp. 249-254 (1979).

König, et al., "Effects of ultraviolet exposure and near infrared laser tweezers on human spermatozoa," Human Reproduction vol. 11 No. 10, pp. 2162-2164 (1996).

PHYWE, Impulscytophotometrie ICP11 Book, pp. 1-24 (1973).

PHYWE, Impulscytophotometrie ICP 22 Datasheet (1976).

Takizawa, et al., "Advancement of the wide-angle JEM-EUSO optical system with holographic and Fresnel lenses," 30th International Cosmic Ray Conference ICRC 2007 Proceedings—Pre-Conference Edition (2007).

Zohdy, et al., "Acoustic Estimation of Thermal Distribution in the Vicinity of Femtosecond Laser-Induced Optical Breakdown," IEEE Transactions on Biomedical Engineering, vol. 53, No. 11, pp. 2347-2355 (2006).

Zohdy, et al., "Optical and Acoustic Detection of Laser-Generated Microbubbles in Single Cells," IEEE Transactions on Ultrasonics, Ferroelectrics, and Frequency Control, vol. 52, No. 1, pp. 117-125 (2006).

Thøgersen, et al., "Reproductive death of cancer cells induced by femtosecond laser pulses," Int. J. Radiat. Biol., vol. 83, No. 5, pp. 289-299 (2007).

Pinkel, et al., "Flow Cytometric Determination of the Proportions of X-and Y-Chromosome-Bearing Sperm in Samples of Purportedly Separated Bull Sperm," Journal of Animal Science 60:1303-1307, (1985).

(56) References Cited

OTHER PUBLICATIONS

Roegener, et al., "Pump-probe detection of laser-induced microbubble formation in retinal pigment epithelium cells," Journal of Biomedical Optics, vol. 9, No. 2, pp. 367-371 (2004).
Lee, et al., "Optical detection of intracellular cavitation during selective laser targeting of the retinal pigment epithelium: dependence of cell death mechanism on pulse duration," Journal of Biomedical Optics, vol. 12, No. 6, pp. 064034-1-064034-14 (2007).
Fulwyler, "Hydrodynamic Orientation of Cells," The Journal of Histochemistry and Cytochemistry, vol. 25, No. 7, pp. 781-783 (1977).
Steinkamp, et al., "Dual-Laser Flow Cytometry of Single Mammalian Cells," The Journal of Histochemistry and Cytochemistry, vol. 27, No. 1, pp. 273-276 (1979).
Balak, et al., "Regenerated Hair Cells Can Originate from Supporting Cell Progeny: Evidence from Phototoxicity and Laser Ablation Experiments in the Lateral Line System," The Journal of Neuroscience, vol. 10, No. 8, pp. 2502-2512 (1990).
Gledhill, et al., "Flow Microfluorometric Analysis of Sperm DNA Content: Effect of Cell Shape on the Fluorescence Distribution," J. Cell. Physiol., vol. 87, pp. 367-376 (1975).
Vogel, et al., "Femtosecond Plasma-Mediated Nanosurgery of Cells and Tissues," Laser Ablation and its Applications, pp. 231-280 (2007).
Lapotko, et al., "Spectral Evaluation of Laser-Induced Cell Damage with Photothermal Microscopy," Lasers in Surgery and Medicine, vol. 36, pp. 22-30 (2005).
Keij, et al., "High-Speed Photodamage Cell Sorting: An Evaluation of the ZAPPER Prototype," Methods in Cell Biology, vol. 42, pp. 371-386 (1994).
Oldfield, "Light Microscopy: An Illustrated Guide," A Mosby Ltd., p. 160 (1993).
Tanabe, et al., "Multiphoton excitation-evoked chromophore-assisted laser inactivation using green fluorescent protein," Natural Methods, vol. 2, No. 7, pp. 503-505 (2005).
Crosland-Taylor, "A Device for Counting Small Particles suspended in a Fluid through a Tube," Nature, vol. 171, pp. 37-38 (1953).
Meistrich, et al., "Resolution of X and Y spermatids by pulse cytophotometry," Nature, vol. 274, pp. 290-291 (1978).
Tirlapur, et al., "Targeted transfection by femtosecond laser," Nature, vol. 418, pp. 290-291 (2002).
Brenner, et al., "Water Immersion Objectives," Nikon Instruments, Inc., Available at http://www.microscopyu.com/articles/optics/waterimmersionobjectives.html (date unknown, accessed Apr. 23, 2009).
White, et al., "Manufacture of Perfluorinated Plastic Optical Fibers," Optical Fiber Communication Conference, Available at http://ieeexplore.ieee.org/xpl/freeabs_all.jsp?arnumber=1362102 (2004).
He, et al., "Targeted photoporation and transfection in human HepG2 cells by a fiber femtosecond laser at 1554 nm," Optics Letters, vol. 33, No. 24, pp. 2961-2963 (2008).
Keu, et al., "Reduced Photoinactivation of 10-Dodecyl Acridine Orange-Sensitized Yeast Cells at High Fluence Rates: Measurements and Computer Simulations," Photochemistry and Photobiology, vol. 60, No. 5, pp. 503-509, (1994).
Mir, et al., "Two-photon absorption of copper tetrasulfophthalocyanine induces phototoxicity towards Jurkat cells in vitro," Photochemical and Photobiological Sciences, vol. 5, pp. 1024-1030 (2006).
Sarkar, et al., "Constancy in Human Sperm DNA Content," Proceedings of the National Academy of Sciences, vol. 71, No. 9, pp. 2512-3516 (1974).
M. Li, "POFnet TM, Plastic Optical Fiber (POF) The Last Few Hundred Meters," Hakko Optical, (2007).
H.M. Shapiro, "Practical Flow Cytometry," John Wiley & Sons, Inc., Available at http://dx.doi.org/10.1002/0471722731.ch8, pp. 266-267 (2003).
Mullaney, et al., "Cell Sizing: A Light Scattering Photometer for Rapid Volume Determination," The Review of Scientific Instruments, vol. 40, No. 8, pp. 1029-1032 (1969).
Merrill, et al. "An Improved Cell Volume Analyzer," The Review of Scientific Instruments, vol. 42, No. 8, pp. 1157-1163 (1971).
Steinkamp, et al., "A New Multiparameter Separator for Microscopic Particles and Biological Cells," Rev. Sci. Instrum., vol. 44, No. 9, pp. 1301-1310 (1973).
Kashima, "Development of Laser Scanning Microscopy Using a Near Ultraviolet Laser," Scanning, vol. 17, pp. 66-69 (1995).
Fulwyler, "Electronic Separation of Biological Cells by Volume," Science, New Series, vol. 150, No. 3698, pp. 910-911 (1965).
Dilla, et al., "Cell Microfluorometry: A Method for Rapid Fluorescence Measurement," Science, New Series, vol. 163, No. 3872, pp. 1213-1214 (1969).
Pinkel, et al., "Sex Preselection in Mammals? Separation of Sperm Bearing Y and "O" Chromosomes in the Vole *Microtus oregoni*," Science, vol. 218, pp. 904-906 (1982).
Kang, et al., "Cancer-Cell Targeting and Photoacoustic Therapy Using Carbon Nanotubes as "Bomb" Agents," Carbon Nanobtubes for Photoacoustic Cancer Therapy, Small 2009, Available at http://www.smalljournal.com (2009).
Abramowitz, et al., "Molecular Expressions Optical Microscopy Primer Specialized Techniques," The Florida State University, Downloaded from http://micro.magnet.fsu.edu/primer/techiques/oblique/obliqueintro.html on Jun. 8, 2009 (Last modified 2003).
Abramowitz, et al., "Molecular Expressions Optical Microscopy Primer Anatomy of the Microscope," The Florida State University, Downloaded from http://micro.magnet.fsu.edu/primer/anatomy/kohler.html on Jun. 8, 2009 (Last modified 2003).
Gledhill et al., "Flow Cytometry and Sorting of Sperm and Male Germ Cells," Flow Cytometry and Sorting Wiley-Liss, (1990) pp. 531-551.
An-Shik Yang et al., "Hydrodynamic Focusing Investigation in a Micro-Flow Cytometer," 9 Biomedical Microdevices 113, 113 (Apr. 2007).
John Sharpe, Flow Cytometry Instrumentation, in Flow Cytometry Educational Guide 2d. Ed., 9 (Dako, 2006).
Howard M. Shapiro, Practical Flow Cytometry (Wiley-Liss, 4th ed. 2003).
Flow Cytometry (Michael G. Ormerod ed., Oxford 3d ed., 2000).
Hercher et al., "Detection and Discrimination of Individual Viruses by Flow Cytometry," 27 Journal of Histochemistry and Cytochemistry pp. 350-352 (1979).
BD FACSCanto II Flow Cytometry Reference Manual, Becton Dickinson and Company (2006).
Johnson, et al., "Flow Sorting of X and Y Chromosome-Bearing Spermatozoa into Two Populations," Gamette Research 16 (1987) pp. 1-9.
Claim Chart Applying Cited Art to All Claims for Which Reexamination is Requested Under 37 C.F.R. 1915(b), Request for Ex Parte Reexamination of U.S. Patent No. 8,004,661 (Control No. 90/009,985, filed Feb. 13, 2012).
Declaration of Daniel Pinkel, Ph.D., filed with Request for Inter-Partes Reexamination of U.S. 8,004,661 (Control No. 95/000,643, filed Aug. 30, 2011).
Declaration of John Sharpe, Ph.D., filed with Request for Ex Parte Reexamination of U.S. Patent No. 8,004,661 (Control No. 90/009,985, filed Feb. 13, 2012).
Decision Granting Inter Partes Reexamination of U.S. Patent No. 8,004,661 (Control No. 95/000,643, filed Dec. 15, 2011).
Office Action in Inter Partes Reexamination of U.S. Patent No. 8,004,661 (Control No. 95/000,643, filed Dec. 15, 2011).
Lindmo et al., "Flow Sorters for Biological Cells," Flow Cytometry and Sorting 145 (Melamed et al., eds., Wiley-Liss 1990).
Johnson et al., "Sex Preselection in Rabbits: Live Births from X and Y Sperm Separated by DNA and Cell Sorting," Biology of Reproduction 41, pp. 199-203 (1989).
Notice of Allowance (mailed Jun. 8, 2011) for U.S. Appl. No. 12/495,406.
Beisker et al., "Double Beam Autocompensation for Fluorescence Polarization Measurements in Flow Cytometry," J. Biophys. vol. 47 (1985) pp. 607-612.

(56) References Cited

OTHER PUBLICATIONS

Request for Inter-Partes Reexamination of U.S. 8,004,661 (Control No. 95/000,643, filed Aug. 30, 2011).
Request for Ex Parte Reexamination of U.S. Patent No. 8,004,661 (Control No. 90/009,985, filed Feb. 13, 2012).
Hung, et al., "Fluorinated Plastics, Amorphous," In *Concise polymeric materials encyclopedia*. J.C. Salamone, ed., CRC Press, Inc., pp. 2466-2476 (1996).
Nakamura, et al., "Characteristics and Use Application of New Fluorine Resin <CYTOP>," Plast. Age. vol. 34, No. 11, pp. 236-239 (Nov. 1988).

* cited by examiner

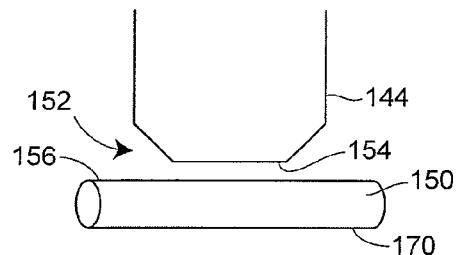
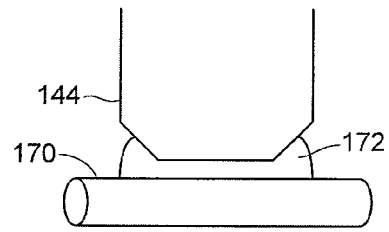
FIG. 9    FIG. 10
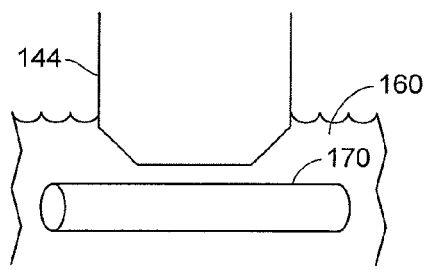
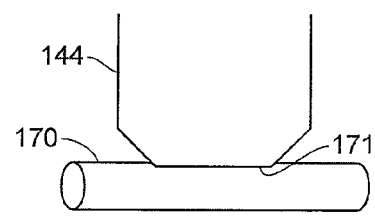
FIG. 11    FIG. 12
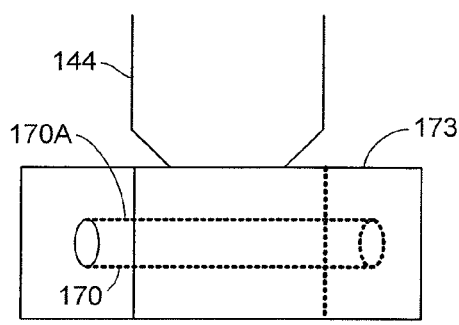
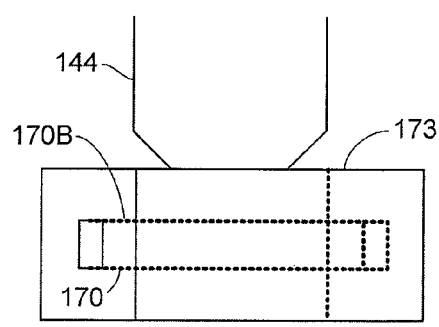
FIG. 13    FIG. 14

METHOD AND APPARATUS FOR LIMITING EFFECTS OF REFRACTION IN CYTOMETRY

RELATED APPLICATIONS

This application is related to concurrently-filed U.S. patent application Ser. No. 12/495,406, the entire disclosure of which is incorporated herein by reference.

FIELD OF THE INVENTION

The present invention relates, in general, to methods and apparatus for performing cytometry and, in particular, to methods for mitigating and/or eliminating the effects of refraction in cytometry systems and apparatus using the method.

BACKGROUND

The term refraction refers to the change in direction of a wave due to a change in the speed of the wave. We encounter the effects of refraction in our day to day life. An object in a pool is not where it appears to be when one attempts to grasp it, or a straw in a glass of water, when observed from outside the glass, appears disjoint. The effects of refraction in these contexts may have little or no practical consequence in one's daily life. However, within the context of a system that analyzes and/or measures radiated waves (e.g., light, sound, etc.), the effects of refraction are particularly important.

A cytometer is one such instrument that analyzes and/or measures radiated waves. Cytometers analyze and/or measure various parameters of the waves to count and/or classify particles or cells. For simplicity, this specification will hereafter use the term "cell," though the principles taught and claimed herein may apply with equal force to other types of particulate matter or discrete bodies. Additionally, the term "objective lens" is used throughout the specification, in accordance with its ordinary meaning, to indicate a lens or combination of lenses that first receives the rays from an object under observation. Further, while the principles taught and claimed herein are described with respect to cytometers and, in particular, with respect to cytometers that measure and/or analyze light waves (i.e., electromagnetic waves with a wavelength between approximately 10 nm and 100 μm), these principles are applicable in any system measuring or analyzing energy exhibiting wave transmission. Still further, the following detailed description describes embodiments utilizing one or more electronic detectors, the output of which a computer or other electronic means analyzes or measures. However, the detector may be other than an electronic detector (e.g., a human eye may be a detector), and the analysis and/or measurement means need not be electronic (e.g., where a brain analyzes light detected by a human eye).

Cytometers analyze and/or measure light by collecting the light through a system of optical elements. The collected light may be light reflected, transmitted, and/or emitted by the object being observed. As just one example, an illumination source (e.g., an ultraviolet illumination source) may illuminate a cell, causing the cell, or a chemical or dye within the cell, to emit light of a different wavelength (e.g., fluorescent light). The optical elements may include lenses, mirrors, filters, and the like, that cooperate to form an optical path. The collected light follows the optical path to a detector (e.g., a photodiode, a human eye, etc.) where the light is analyzed and/or measured. In the example above, the detector may detect a peak in the received light for each cell in or passing through a detection/interrogation area, and a computer may count the peaks to determine the number of cells. Alternatively, or in addition, the detector may detect different amounts or types of light corresponding to different cells, and a computer may interpret or analyze signals received from one or more detectors.

The various optical elements through which a cytometer collects light typically include a variety of materials (e.g., glass lenses, plastic filters, crystalline materials, metallic surfaces, etc.). Moreover, in traversing the entirety of the optical path, from the origin of the light to a detector, the light may pass through any number of materials and/or environments. For example, fluorescent light emitted from a stain attached to deoxyribonucleic acid (DNA) of a cell may pass through: various materials within the cell; a cell membrane; a buffer solution and/or cell medium in which the cell is suspended and/or bathed; a cover slip or other container material; a fixing agent; water; oil; air; a glass lens, etc. Each of these materials may have different properties with regard to the light waves incident upon the material, which properties may affect the speed of the light waves through the material and, ultimately, the path of the light. In short, refraction occurring at the interfaces of the various materials in the optical path of a cytometer can alter the path of light collected to image the analyte. (Of course, refraction may also affect illumination light directed toward the analyte.) The effect of such alterations in the path of the collected (or transmitted) light may include a reduction in the peak power or intensity of incident or imaging light delivered to or emitted from the analyte in a focus series across the analyte. Similarly, power or intensity profile in a focus series may broaden, reflecting an increase in the effective focal volume for the system.

One of the properties of a material is the refractive index. The refractive index is a number that indicates the speed of light in a given medium as either the ratio of the speed of light in a vacuum to that in the given material (i.e., an absolute refractive index) or the ratio of the speed of light in a specified medium to that in the given medium (i.e., a relative refractive index). Unless otherwise specified, refractive indices within this specification are absolute refractive indices.

Solids and liquids generally have particularly large differences in their refractive indices. For example, the refractive index of water (which varies by temperature and wavelength) is in the range 1.331-1.345 at 20° C. Buffers for use in cytometry typically contain dissolved salts and other chemicals and have a refractive index similar to or higher than water alone. Such buffers are typically used to contain and/or transport cells that are the subject of the analysis (the 'analyte'). Materials used to construct elements of the optical path, such as an optical cell, include glasses, plastics, and crystalline materials, of which some examples may include acrylic, polycarbonate, quartz, sapphire glass, polystyrene, polypropylene, and/or other materials. Each of these solid materials typically has a refractive index significantly different from (and usually greater than) that of water.

Well known to those skilled in the art of optical system design and construction are various approaches to ameliorating aberrations arising from the shape, position, and optical properties of the various elements of optical systems. Such systems include, by way of example but not exclusion, telescopic systems, microscope systems, and imaging systems. Optical system design frequently involves the selection of materials, numbers and shapes of optical elements (where the figuring of optical elements of differing complexity is associated with different costs), and configurations, where the requirements of the system are assessed against the cost of achieving optical performance that suffices to carry out the desired function. For example, a telescope that produces images for visual observation may perform satisfactorily despite the presence of chromatic aberrations induced by the different refraction angle of light of different wavelengths as it passes through the lenses of the system. However, additional optical elements may be required to reduce or eliminate chromatic aberration in a similar telescope intended for precise astronomical photography. Furthermore, as another example, in telescopes and other optical systems, specially shaped lenses may be introduced to compensate for systematic aberrations introduced in the imaging of the object of study by the use of other elements that are ground to spherical curves, an aberration known as spherical aberration. Furthermore, in yet another example, optical systems may be designed that correct for specific and well-understood aberrations that occur outside of the lenses and other conventional components of the constructed optical system. For instance, water immersion type microscope compound objective lenses are now produced that correct for aberrations in the optical path in imaging an object lying beneath a cover slip and a layer of water, where the optical system is designed to correct for the refraction of light at both sides of the cover slip. Such corrective design may offer improved focus and resolution relative to optical systems that do not correct for systematic aberrations introduced by the properties of the materials through which the imaging light passes before entering the objective lens.

The possibility of designing an optical system to compensate for aberrations that are internal to the optical system, or for aberrations that occur as a result of materials that are part of or near to the object being imaged, in no way reduces the fact, well understood to those skilled in the art, that it is desirable to reduce or eliminate such aberrations where possible. By way of example, oil immersion, where the space between the objective lens of the microscope and the cover slip of the sample is filled with an oil having a refractive index matching that of the coverslip glass, is commonly used in microscopy to reduce or eliminate the refraction that would occur at the air-coverglass interface in the absence of the oil. In practice, some aberrations that are introduced by materials and apparatus through which imaging light must be collected are not readily or affordably corrected in the design of an optical system. By way of example only, liquid jet-in-air cytometers feature a roughly cylindrical jet of aqueous fluid containing cells that are the object of study. Lenses to correct for aberrations caused by the interface of the aqueous cylinder with the surrounding air have not been developed, since the expense and technical difficulty of designing such lenses is high. Nevertheless, those skilled in the art of cytometry will appreciate that cytometers with enclosed liquid streams featuring flat transparent walls through which imaging light is collected, may feature improved imaging, signal strength, focus, and/or resolution by virtue of reduced optical aberration.

FIGS. 1 and 2 illustrate the problem that results from the boundaries between materials having different refractive indices. FIG. 1 depicts a typical microscope objective 10. The microscope objective 10 acts to focus light waves 12 passing through the microscope objective 10 to a nominal focal point (NFP) 14. FIG. 2 depicts the same microscope objective 10. A cover slip 16, such as a cover slip 16 that may be used with a microscope slide (not shown), is disposed in between the objective lens 10 and the NFP 14. The cover slip 16 is a solid material (e.g., glass or plastic) having a refractive index higher than that of a medium 18 (e.g. air) on either side of the cover slip 16. The refractive index change occurring at an interface 20 of the cover slip 16 and the medium 18, and the refractive index change occurring at an interface 22 of the cover slip 16 and the medium 18, result in a shift in the position of the NFP 14 away from the lens 10. The modified focal point is referred to as an Actual Focal Position (AFP) 24. The AFP 24 is not a point but a region or volume in space, due to aberration induced by the refractive index changes in the media. The aberration may be characterized as a point spread function for the system and may be calculated numerically. As a consequence of the aberration of the AFP 24, the peak intensity of light measured in a focus series (focusing through a sample located at a defined position) is reduced, and the full-width half maximum of the distribution is broadened.

In confocal microscopy there exists an alternative to using a specially designed optical system to mitigate the effects of refraction. U.S. Pat. No. 5,406,421 describes a coverslip for use in a confocal microscope. The coverslip is made of a transparent material having a refractive index which is lower or higher than that of water by 0.02 or less. In particular, the coverslip is made of a transparent fluorocarbon resin having a refractive index of approximately 1.34. When combined with a water-dipping objective lens, the use of such a coverslip can greatly decrease the deterioration of focusing accuracy of a confocal microscope. However, in cytometry, it may be impractical to use a specially-designed objective lens. For example, a cytometer requiring a specially-designed objective lens may prove too costly relative to competing devices or for a given application. Moreover, in some instances, particularly in flow cytometry, it may be impractical to use a coverslip, regardless of the material from which the coverslip is made, because, for example, a flat surface along any side of the flow path may detrimentally affect the orientation or the flow of the analyte through the flow path. Moreover, the use of a specially-designed coverslip, if possible, may prove insufficient to correct aberration in cytometry applications. For example, in some cytometer configurations, such as the flow cytometer described below with respect to FIGS. 3 and 5, elements other than a coverslip, such as the walls of a flow path, may cause focal aberrations.

Regardless of the cause of the focal aberration, the loss of peak intensity and the dispersion of the focus causes a reduction in resolution and in the signal to noise ratio for the collected light or image. As a consequence, light or an image may fail to be resolved, or properties of them may be insufficiently distinct against the background noise of the system. An example of such a property is the fluorescence of a fluorescent-dye labeled cell. A reduction in the amount of light collected from such a cell due to aberration in the AFP 24 may raise the detection threshold for the measurement of such light, and may decrease the precision with which the fluorescent light is measured. This represents a reduction in the efficiency of the optical system as a whole and has practical implications for cytometry and for the design of a cytometry system. By way of example, the implications may require any or all of the following:

Increased observation time for the sample;
Reduced sample rate (analytes per unit time);
Incorporation of more and/or brighter fluorochromes (for fluorescent samples);
More intense excitation light for (to cause fluorochrome excitation);
More sensitive photodetector(s);
Higher numerical aperture of objective lens(es); and
Lower optical and/or electronic background noise.

These requirements may have the effect of increasing the cost of a cytometer, and/or decreasing the throughput or analysis speed of the cytometer, and/or changing the type or expense of fluorochromes, samples, or other components that may be used for a specific purpose in a cytometer.

The situation illustrated in FIG. 2 represents a simple geometry having flat interfaces 20 and 22 between the medium 18 and the cover slip 16. Other geometries may be desirable in the design of a cytometer and may cause additional aberration in the AFP. For example, a flow path having a circular cross section provides desired benefits in a flow cytometer (i.e., a cytometer that measures an analyte as the analyte flows past or through a detection/interrogation region) and, in particular, in a flow cytometer used to sort mammalian sperm cells. Of course, curvature at a boundary between two media having different refractive indices (e.g., an aqueous analyte-bearing medium and a flow path in which the aqueous medium flows) will introduce additional aberration in the light path.

Further, the flow path itself may introduce more than two interfaces between materials with different refractive indices. FIG. 3 illustrates one configuration for a flow cytometer, in which configuration an objective lens 26 is oriented coaxially with a flow 28 bearing an analyte 30. For reasons explained in greater detail in co-pending application Ser. No. 12/495,406, the configuration depicted in FIG. 3 may be preferable over other flow cytometer configurations, especially in situations in which the analyte is a mammalian sperm cell, the viability of which sperm cell must be maintained. As FIG. 3 illustrates, the analyte 30 flows within a flow path 31 toward the objective lens 26, and through a nominal focal point 32, before being diverted by a transverse flow 34 into an exit path 36. Walls 38 and 40 of the flow path 31 may be made of like or dissimilar materials, and typically have a refractive index different from an aqueous solution (not shown) bearing the analyte. The aberration of the AFP in such a situation will be complex due to the fact that rays between the NFP 32 and the objective lens 26 must pass through the walls 38 and 40 of the flow path 31. Current cytometers may avoid this problem, in part, by situating the optical pathway and, in particular, the NFP, such that the walls 38 and 40 of the flow path 31 do not interfere with the optical path.

The use of "water immersion" or "water dipping" objective lenses may, in part, correct aberration caused by the collection of light through a parallel-sided wall or cover slip and/or a fluid. Water immersion objective lenses correct for an optical path that passes through a liquid medium and a determined thickness of a medium of a higher refractive index, typically a glass cover slip. However, even variations in cover slip thickness smaller than the tolerances to which cover slips are typically manufactured can cause the AFP to vary from the NFP. Further, the determined cover slip thickness for which a water immersion objective lens is designed limits the design of any optical cell in which a flow path may be formed. FIG. 4 illustrates a water immersion objective lens 44 having a nominal focal point 32. A tip 45 of the water immersion objective lens 44 sits in water 46 on a glass coverslip 47 of a determined thickness. An aqueous medium 49 (which may be water) having the same refractive index as the water 46 is below the coverslip 47. Contrasted with water immersion objective lenses, water dipping objective lenses are fully corrected for imaging in water without an intervening cover slip.

Moreover, even a cytometer employing a corrected objective lens, such as a water dipping or a water immersion objective lens, remains subject to refractive effects in many instances. For example, FIG. 5 depicts a cytometer 50 in which glass 42 forms the flow path 31. As will be appreciated, the cytometer 50 includes a number of interfaces between different materials, including a glass-immersion fluid interface 51, an immersion fluid-cover material interface 53, a cover material-analyte medium interface 55, and analyte medium-flow path wall interfaces 57 and 59. As in FIG. 4, the tip 45 of the water immersion objective lens 44 sits in water 46. Unlike FIG. 4, the water 46 in FIG. 5 sits on a top thickness 48 of the flow path 31, which top thickness 48 is the same as that of the coverslip 47 depicted in FIG. 4, and corresponds to the thickness for which the water immersion objective lens 44 is corrected. Accordingly, light 52 passing between the water immersion objective lens 44 and the NFP 32 without intersecting the walls 38 and 40 of the flow path 31 remains in focus. However, the glass 42 forming the walls 38 and 40 refracts light 54 that intersects the walls 38 and 40 at the interfaces 57 and 59, causing aberration from the NFP.

It is an objective of the presently described methods and apparatus to mitigate and/or eliminate refractive effects in cytometric devices and methods.

SUMMARY

The present specification describes methods and apparatus for performing cell cytometry, which methods and apparatus mitigate or eliminate the effects of refraction that result from interfaces between materials having different refractive indices. In some embodiments, a cytometer includes a flow path having an input, an output, and a detection region. An excitation energy source excites a molecule or molecules in an analyte and a detector detects the resulting energy. A processor, coupled to the detector and to a memory device interprets a signal from the detector. An objective lens has a focal point in the detection region. The focal point and the objective lens define a virtual conical volume. At least a portion of a component disposed wholly or partially within the virtual conical volume, or disposed at least partially within a volume through which light from the focal point passes between the focal point and the optical focusing element, comprises a material having a refractive index in the range of 1.30 to 1.40 inclusive.

In some embodiments, the material with the refractive index in the range of 1.30 to 1.40 inclusive is one of a perfluoroalkoxy polymer, an amorphous fluoropolymer; and an amorphous perfluoropolymer.

In some embodiments, the objective lens is a corrected objective lens and, in particular, is one of a water dipping objective lens, a water immersion objective lens, or an oil immersion objective lens.

In some embodiments, a volume defined by an objective lens and a focal point associated with an objective lens includes a material having a refractive index between 1.30 and 1.40 inclusive. In some embodiments, the material forms at least a portion of one or more of the group consisting of an optical cell, a window, a cuvette, a tube, a passage, a chamber, a slide, a wall, and a boundary.

In alternate aspects, the cytometer is a scanning cytometer, an imaging cytometer, or a flow cytometer.

In some embodiments, the objective lens is in contact with one of a buffer solution, a sheath fluid, a growth medium, and a fluid used to carry, suspend, or bathe the analyte. Similarly, in some embodiments, the material with the refractive index between 1.30 and 1.40 inclusive is in contact with one of a buffer solution, a sheath fluid, a growth medium, and a fluid used to carry, suspend, or bathe the analyte.

In some embodiments, a method of performing cytometry includes adjusting the refractive index of a first material such that the difference between the refractive index of the first material and the refractive index of a second material is less than 0.02. In some embodiments, the first material is used to carry the analyte, suspend the analyte, or bathe the analyte. In particular, the first material may be one of a buffer solution, a sample fluid, a sheath fluid, a growth medium, and a lens immersion fluid. Further, in some embodiments, the second material is one of an optical cell, a window, a cuvette, a tube, a passage, a chamber, a slide, a wall, and a boundary.

In some embodiments, the second material has a refractive index between 1.30 and 1.40 inclusive and, in particular, the second material may be one of a perfluoroalkoxy polymer, an amorphous fluoropolymer; and an amorphous perfluoropolymer.

BRIEF DESCRIPTION OF THE FIGURES

FIG. 9 depicts an embodiment of a flow cytometer, according to the described methods and apparatus, in which the cells flow through a tube;

FIG. 10 depicts an alternate embodiment of the flow cytometer of FIG. 9;

FIG. 11 depicts another alternate embodiment of the flow cytometer of FIG. 9;

FIG. 12 depicts yet another alternate embodiment of the flow cytometer of FIG. 9;

FIG. 13 depicts an embodiment of a flow cytometer, according to the described methods and apparatus, in which the cells flow through a tube formed in a cuboid;

FIG. 14 depicts an alternate embodiment of the flow cytometer of FIG. 13;

DETAILED DESCRIPTION

The present specification describes methods and apparatus for performing cytometry and, in particular, methods and apparatus that minimize or eliminate the effects of refraction in cytometry systems and apparatus using the methods. Unless otherwise defined, all technical and scientific terms used herein have the same meaning as commonly understood by one of ordinary skill in the art to which the claimed inventions belong.

Figure 6A:
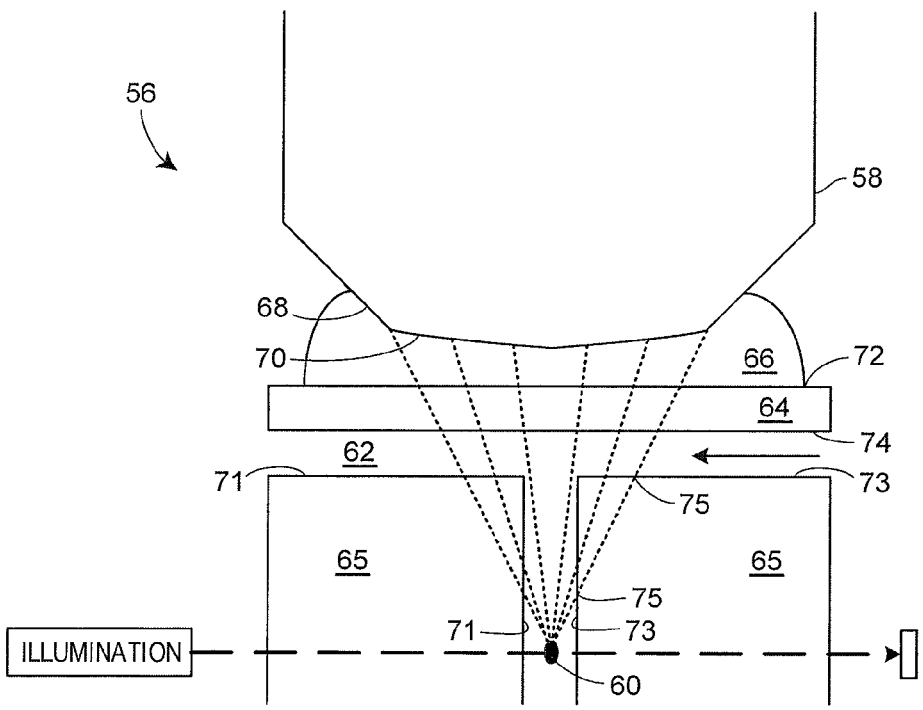
FIG. 6A illustrates an advantage of a flow cytometer implementing the presently described methods and apparatus over the flow cytometer of FIG. 5A.

FIG. 6A depicts a portion 56 of an embodiment of a cytometer according to the described apparatus and/or employing the described methods. An objective lens 58 has a nominal focal point 60 in an analyte medium 62 bearing an analyte, (not shown) such as a population of biological cells, disposed at or around the nominal focal point 60. The analyte may flow past the nominal focal point 60 (as in the flow cytometer illustrated in FIG. 6A) or may be disposed on a surface (as in scanning and/or imaging cytometry) or in suspension such that the analyte is generally in the same focal plane as the nominal focal point 60. A solid cover medium 64, illustrated as a top wall of a flow path in the portion 56, sits between the objective lens 58 and the nominal focal point 60. The solid cover medium 64 may be, by way of example and not limitation, a cover slip, the top of a Petri dish, a top surface of a flow path, a top surface of an optical cell (e.g., a cuvette) in which a flow path is formed, a window in a material forming a flow path, a chamber, a microscope slide, a transparent boundary material, etc. A lens immersion medium 66 may be disposed between the objective lens 58 and the solid cover medium 64 such that a tip 68 of the objective lens 58 is in contact with the lens immersion medium 66. Thus, there exists in FIG. 6A at least four physical interfaces between differing materials. A first interface 70 exists between the objective lens 58 and the lens immersion medium 66, a second interface 72 exists between the lens immersion medium 66 and the solid cover medium 64, a third interface 74 exists between the solid cover medium 64 and the analyte medium 62, and additional interfaces 75 may exist between the analyte medium 62 and other portions of the cytometer, such as flow path walls 71 and 73, which may be formed of a medium 65, which may, in some embodiments, be the same as the medium 64. Each of the interfaces 70, 72, 74, and 75 presents an opportunity for refraction to occur (and thus an opportunity to mitigate such refraction) if the respective refractive indices of the materials forming the interface 70, 72, 74, or 75 differ.

Referring still to FIG. 6A, the solid cover medium 64 and the medium 65 forming the flow path walls 71 and 73 are formed of a material having a refractive index between 1.30 and 1.40 inclusive, and one or both of the immersion medium 66 and the analyte medium 62 has a refractive index between 1.30 and 1.40 inclusive. For example, the analyte medium 62 and/or the immersion medium 66 may be water or other similar fluid having a refractive index in the range of 1.33 to 1.35. In particular, the analyte medium 62 may be any liquid used to carry the analyte, suspend the analyte, or bathe the analyte including, but not limited to: a buffer solution, a sample fluid, a sheath fluid, or a growth medium. The solid cover medium 64, meanwhile, may be formed of a perfluoroalkoxy polymer, an amorphous fluoropolymer, an amorphous perfluoropolymer, or other such materials having a refractive index between 1.30 and 1.40 inclusive. By way of example and not limitation, the solid cover medium 64 may be formed of Cytop™, manufactured by Asahi Glass Co., Ltd., Teflon® AF, manufactured by DuPont™, or Teflon® PFA, also manufactured by DuPont™, which have refractive indices of approximately 1.34, 1.31-1.33, and 1.34-1.35, respectively.

Figure 6B:
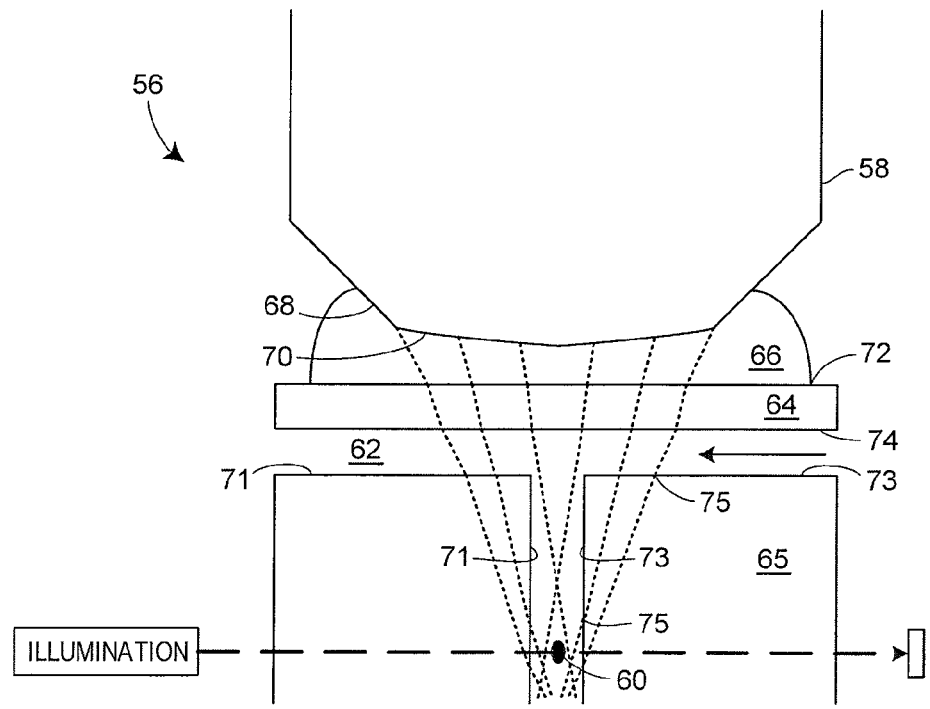
FIG. 6B illustrates an advantage of a flow cytometer implementing the presenting described methods and apparatus over the flow cytometer of FIG. 5A.

Of course, one need not achieve an exact match between the materials forming one of the interfaces 70, 72, 74, and 75. For example, at the interface 74, the analyte medium 62 may have a refractive index around 1.35 (e.g., water), while the cover medium 64 may have a refractive index around 1.34 (e.g., Cytop™). In such instance, depicted in FIG. 6B, the relatively small differences between the media 62 and 64 forming the interface 74, the media 64 and 66 forming the interface 72, and the media 62 and 65 forming the interfaces 75, provides a marked improvement over the prior art, in which the cover medium 64 generally is formed of glass having a refractive index in the range of 1.47 (Pyrex® glass) to 2.04 (arsenic trisulfide glass) or plastic having a refractive index in the range of 1.46 to 1.55. Moreover, one need not improve the match of the refractive indices of the materials at each of the interfaces 70, 72, 74, and 75, as improving the match of the refractive indices of the materials at even one of the interfaces 72 and 74 will improve the performance of the cytometer.

Further, in instances in which the refractive index of the material forming the cover medium 64 does not precisely match the refractive index of the analyte medium 62 (or of the immersion medium 66), one may adjust the refractive index of the analyte medium 62 (or of the immersion medium 66). As just one example, if the cover medium 64 is formed of Cytop™ with a refractive index of 1.34, and the analyte medium 62 is water with a refractive index of 1.33, one may adjust the refractive index of the water (e.g., by adding salts) to better match the refractive index of the Cytop™. Though not required, it is preferable to adjust the refractive index of the analyte medium 62 (or of the immersion medium 66) to be within 0.02 of the refractive index of the cover medium 64.

Figure 7:
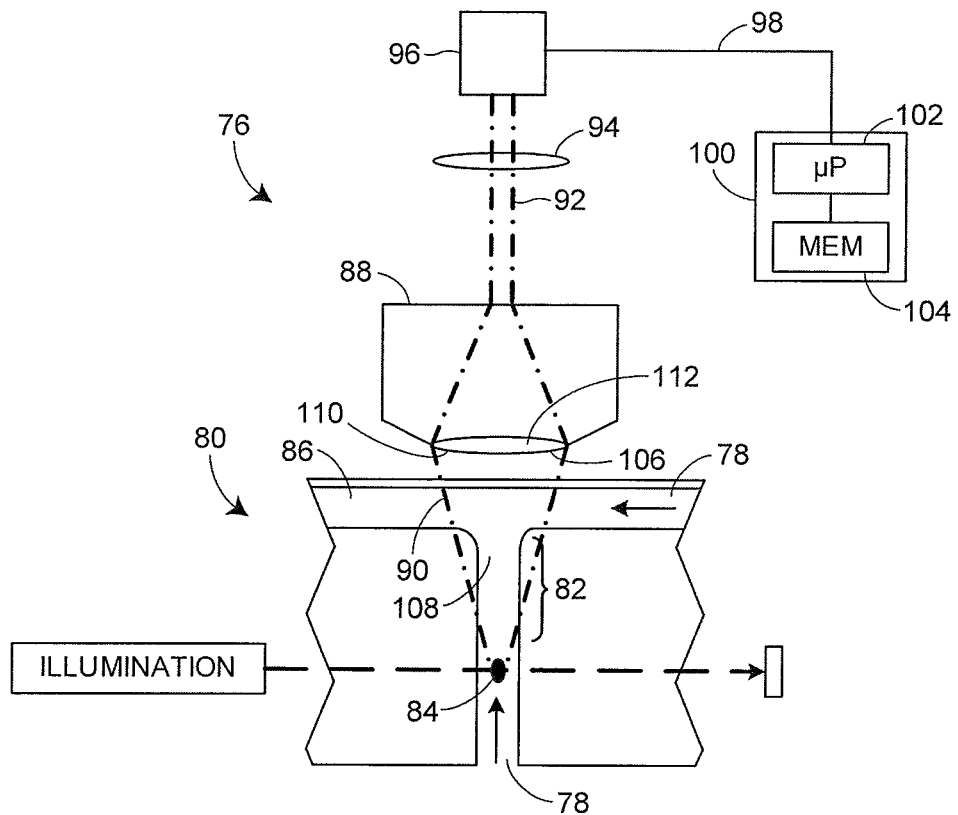
FIG. 7 depicts an embodiment of a flow cytometer in accordance with the described methods and apparatus.

FIG. 7 depicts a flow cytometer 76 in accordance with one or more of the described methods and apparatus. The cytometer 76 includes a flow path 78 that passes, at least partially, through a cuvette 80. An interrogation region 82 includes a portion of the flow path 78, which portion of the flow path 78 includes a nominal focal point 84. Of course, the interrogation region 82 may include a portion of a transverse flow 86 in the flow path 78. An objective lens 88 focuses light or other energy 90 collected from the nominal focal point 84, resulting in focused energy 92. The focused energy 92 may interact with one or more optical elements, such as a filter 94, before arriving at a detector 96. The detector 96 detects the focused energy 92, and may send a signal representative of the energy 92 over a connection 98 to a controller 100. The controller 100 may include, for example, a processor 102 and a memory 104.

Figure 8:
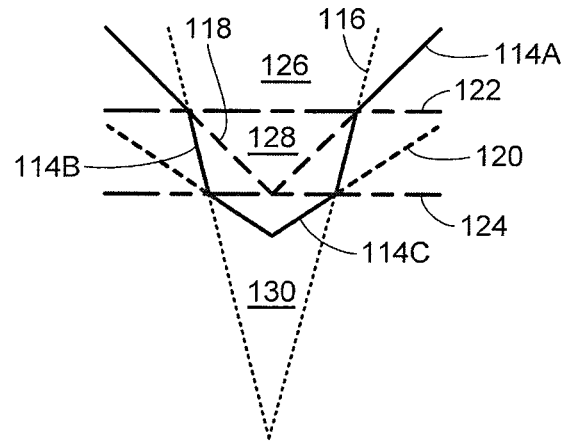
FIG. 8 depicts an embodiment of a conical volume between a focal point and an objective lens, and including materials of different refractive indices, in accordance with the described methods and apparatus.
Figure 15:
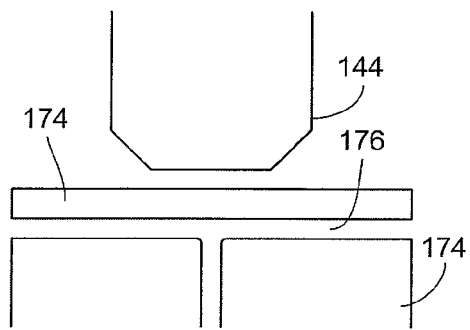
FIG. 15 depicts an embodiment of a flow cytometer, according to the described methods and apparatus, in which the analyte flows through a flow path formed in a body.
Figure 16:
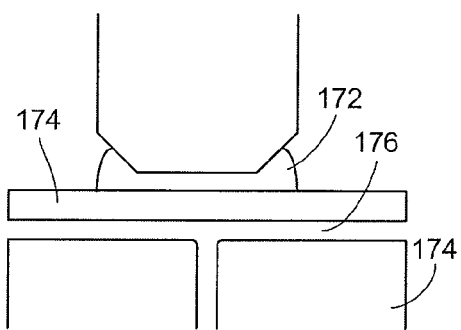
FIG. 16 depicts an alternate embodiment of the flow cytometer of FIG. 15.

As generally known in the art, one or more lens elements 106 (e.g., a hemispherical front lens, a meniscus lens, etc.) act to create the nominal focal point 84. The nominal focal point 84 defines the apex of a generally conical volume 108 between the nominal focal point 84 and an outer element 110 of the objective lens 88 forming a base 112 of the conical volume 108. The conical volume 108 may be a right circular conical volume, but may also be an oblique conical volume. Further, the conical volume 108 may be formed of sections 114A, 114B, and 114C of multiple cones 116, 118, and 120 joined together, as illustrated in FIG. 8, such as is the case where one or more interfaces 122 and 124 are formed of materials 126, 128, and 130 having differing refractive indices. Moreover, the volume 108 need not be precisely conical, but may generally include the volume through which energy passes between the focal point 84 (or an actual focal point) and the objective lens 88.

While FIG. 7 depicts the flow cytometer 76 as having the objective lens 88 generally coaxially aligned with the flow path 78 in the interrogation region 82, one could employ the presently described methods and apparatus in flow cytometers having other configurations. For example, the presently described methods and apparatus may be employed in a flow cytometer 76 in which the objective lens 88 is generally perpendicular to the flow path 78 in the interrogation region 82, or a flow cytometer 76 in which the objective lens 88 is at an oblique angle to the flow path 78 in the interrogation region 82. Moreover, in the flow cytometer 76, the flow path 78 need not pass through the cuvette 80, but may instead or additionally pass through an optical cell, a tube, a passage, a chamber, etc., any of which may be formed of a material having a refractive index between 1.30 and 1.40 inclusive.

FIGS. 9-14 show various embodiments of flow cytometers using the methods and apparatus described herein. In each, an objective lens 144 operates to focus light from an analyte (not shown). As described above, the methods and apparatus may mitigate and/or eliminate refraction due to interfaces between materials having different refractive indices in various configurations. The objective lens 144 observes the analyte (not shown) flowing through a tube 170 that forms a flow path. An analyte fluid 150, suspending or carrying the analyte, may flow through the tube 170. Of course, the tube 170, while depicted in FIGS. 9-13 as a right circular cylinder, need not have a circular cross-section and, in fact, need not be cylindrical at all. Instead, the tube 170 may have a rectangular cross-section, as depicted in FIG. 14. In accordance with the methods and apparatus described, the tube 170 may be formed of a material having a refractive index similar to or the same as either or both of a fluid (not shown) flowing through the tube 170, an immersion fluid 172 in which the objective lens 144 is immersed (FIG. 10), or a dipping fluid 160 in which the objective lens 144 is dipped (FIG. 11). In particular, the tube 170 may be formed from one of a perfluoroalkoxy polymer, an amorphous fluoropolymer, or an amorphous perfluoropolymer, or other such material having a refractive index between 1.30 and 1.40 inclusive.

FIG. 9 depicts an embodiment in which the objective lens 144 does not contact the tube 170. Instead, a volume of air 152 exists between the objective lens 144 and the tube 170. Accordingly, in the embodiment depicted in FIG. 9 there remains at least an interface 154, between the objective lens 144 and the air 152, and an interface 156, between the air 152 and the tube 170. Thus, while refraction may still affect the optical system, the system operates to reduce the refractive effects because the refractive indices of the analyte fluid 150 and the tube 170 may be the same or approximately the same (e.g., within 0.02).

If the objective lens 144 depicted in FIG. 9 was in contact with the tube 170, both of the interfaces 154 and 156 could be eliminated. In one aspect of the embodiment, light passing between the analyte fluid 150 and the objective lens 144 passes through media having identical (or at least similar) refractive indices. For example, and without limitation, the analyte fluid 150 may have a refractive index close to or equal to that of water (e.g., 1.33) and the tube 170 may be formed of Cytop™, with a refractive index of 1.34. Moreover, in accordance with the methods described herein, the refractive index of the analyte fluid 150 may be adjusted to match the refractive index of the tube 170 such that the refractive indices of both the analyte fluid 150 and the tube 170 are about 1.34.

In the depiction of FIG. 10, the objective lens 144 is a water (or oil) immersion objective lens, in contact with the immersion fluid 172 (e.g., water or oil) disposed between the objective lens 144 and the tube 170. In instances where the immersion fluid 172 has the same or similar refractive index as the tube 170 and/or the analyte fluid 150, the refractive effects may be minimized. For example, and without limitation, the immersion material 172 and/or the analyte fluid 150 may be water or other fluids having (or adjusted to have) a refractive index of 1.34, and the tube 170 may be formed of Cytop™ also having a refractive index of 1.34.

The embodiment depicted in FIG. 11 substitutes for the objective lens 144 a water dipping objective, and substitutes a dipping fluid 160 (e.g., water) for the immersion fluid 172. Of course, either or both of the dipping fluid 160 and the immersion fluid 172 may be the same as the analyte fluid 150. For example, in one embodiment, the analyte fluid 150 may be a buffer solution, and may also be the same fluid used as the immersion fluid 172 or the dipping fluid 160.

In some embodiments, a tip 171 of the objective lens 144 forms a portion of the tube 170 (FIG. 12), eliminating at least the interface between the tube wall and the analyte fluid 150, and the interface between the tube wall and the objective lens 144. In some embodiments, the tube 170 may be formed or embedded in a cuboid, a cylinder, or other generally prismatic shape. FIGS. 13 and 14, respectively, depict a cylindrical tube 170A and a rectangular tube 170B embedded or formed within a cuboid 173.

Figure 1:
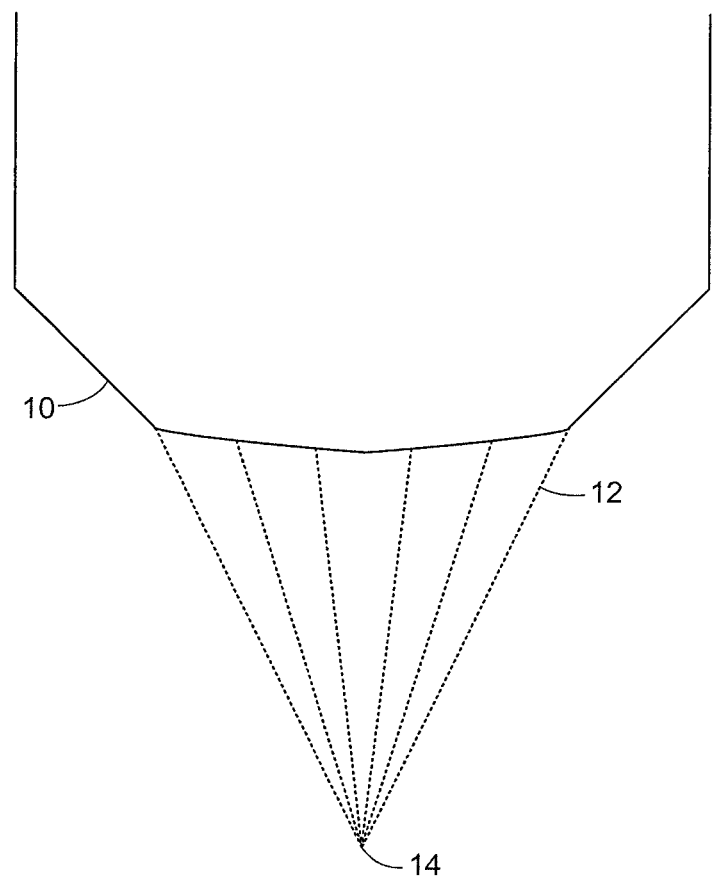
FIG. 1 depicts a nominal focal point of an objective lens.
Figure 2:
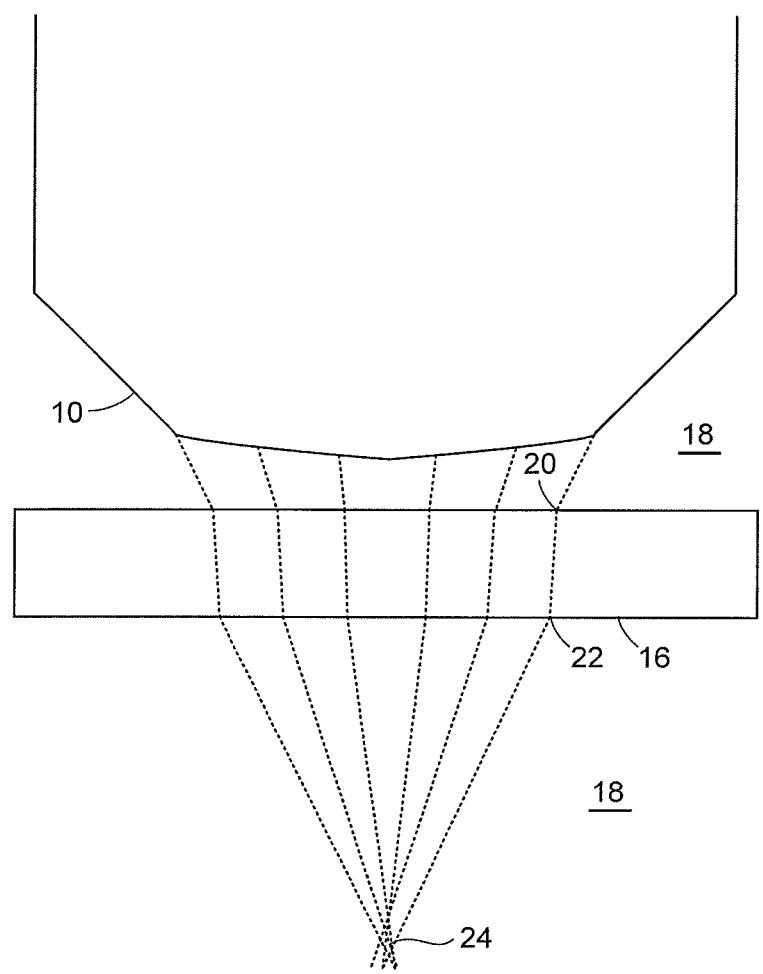
FIG. 2 depicts focal distortion caused by the placement in the optical path of a two interfaces between materials of different refractive indices.
Figure 3:
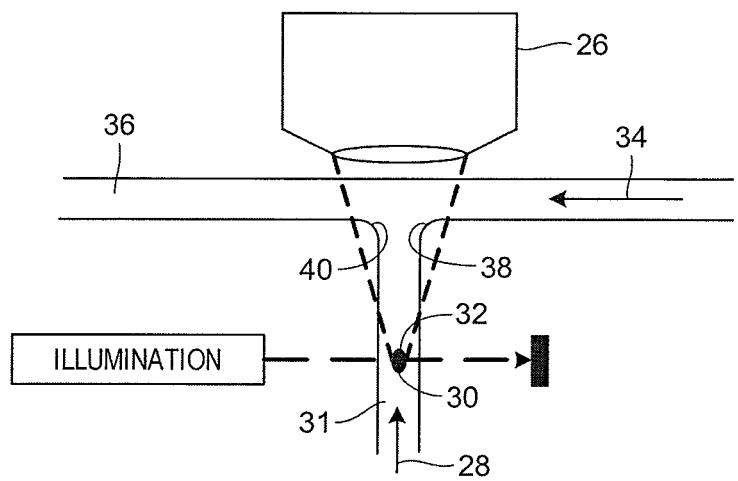
FIG. 3 depicts an embodiment of a flow cytometer in accordance with the presently described methods and apparatus.
Figure 4:
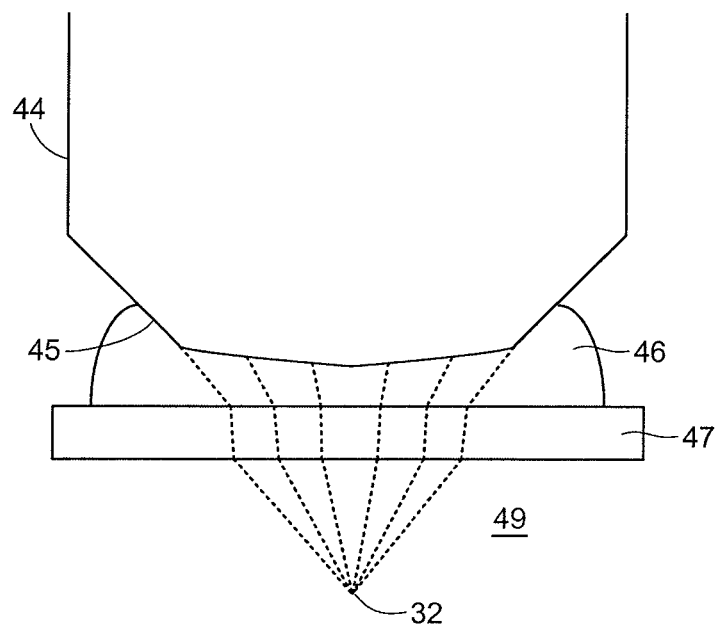
FIG. 4 depicts a water immersion objective lens in accordance with the presently described methods and apparatus.
Figure 5:
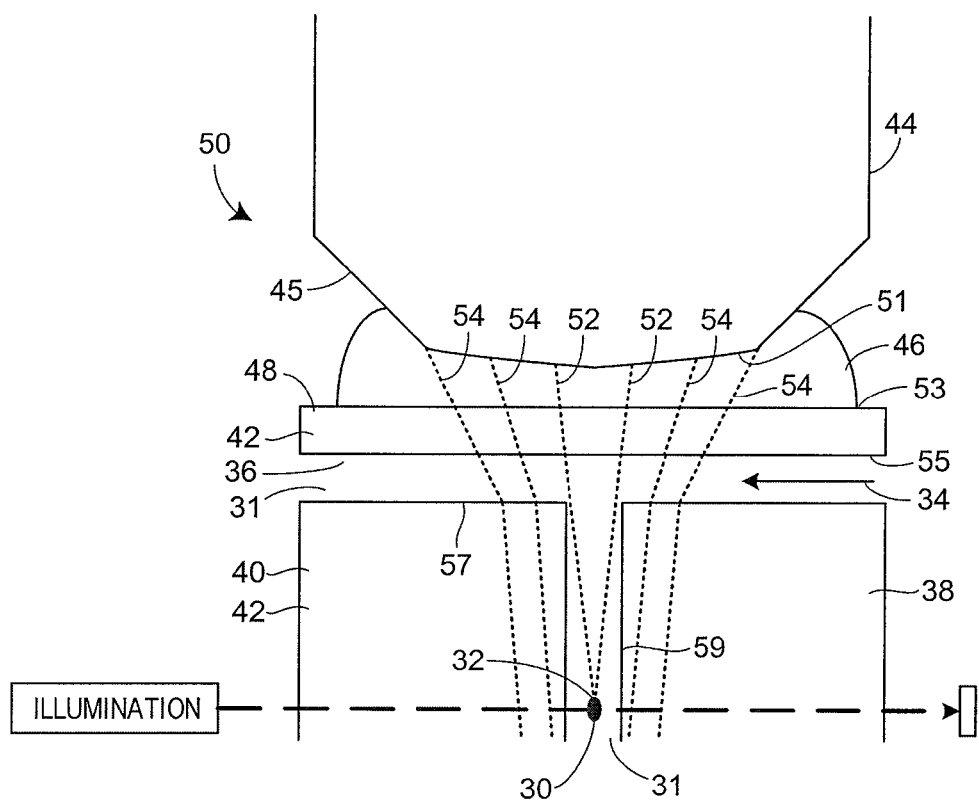
FIG. 5 illustrates the effects of refraction on the focal volume of a known flow cytometer.

As will be appreciated, the embodiments depicted in FIGS. 9-14 mitigate or eliminate the effects of refraction as light passes through the various materials between the analyte and the objective lens 144. For example, these embodiments, as well as others, may improve greatly flow cytometry systems employing optical elements oriented orthogonally, or at approximately right angles, or at oblique angles with respect to the axis of flow of cells, in addition to flow cytometry systems employing coaxial detection (as depicted in FIG. 3). It is well known that, with respect to the flow of cells through the flow path of a flow cytometer, a flow path with a curvilinear cross-section (such as a cylinder) may be preferable over a flow path with a rectangular cross-section in some applications. However, it is likewise well known that, in flow cytometers employing orthogonal detection, the curvilinear flow path walls of such a flow path introduce focal aberration due to refraction occurring at least at the interface of the medium carrying the cells and the flow path wall. The described methods and apparatus mitigate the refractive effects of at least that interface, and possibly others, by matching the refractive indices of the various materials at the interface.

Figure 17:
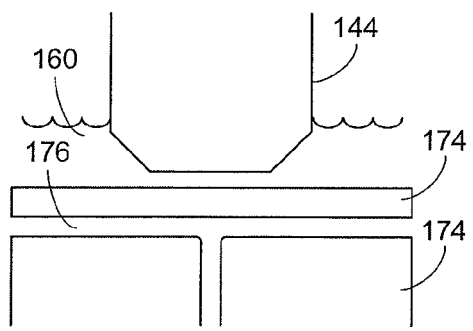
FIG. 17 depicts another alternate embodiment of the flow cytometer of FIG. 15.
Figure 18:
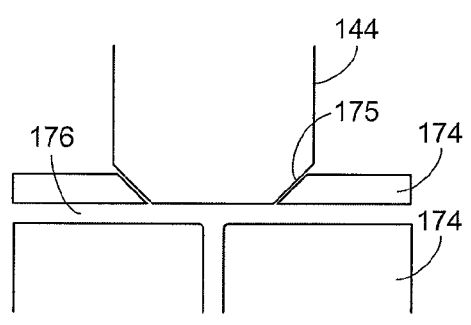
FIG. 18 depicts yet another alternate embodiment of the flow cytometer of FIG. 15.

FIGS. 15-18 depict embodiments similar to those depicted by FIGS. 9-12 and, like the FIGS. 9-12, are adapted for use with a flow cytometer. In FIGS. 15-18, the objective lens 144 observes an analyte (not shown) flowing through a body 174 in which a flow path 176 is formed. While the figures depict the flow path 176 as a "T" intersection, the flow path 176 may, instead, form an inverted "L" as depicted, for example, in FIGS. 19 and 20. In accordance with the methods and apparatus described, the body 174 may be formed of a material having a refractive index similar to or the same as either or both of a fluid (not shown) flowing through the flow path 176, a fluid 172 in which the objective lens 144 is immersed (FIG. 16), or a fluid 160 in which the objective lens 144 is dipped (FIG. 17). Alternatively, the objective lens 144 may form a portion of the flow path 176, protruding into the body 174 through an opening 175, as depicted in FIG. 18. In this manner, the embodiments depicted in FIGS. 15-18 mitigate or eliminate the effects of refraction as light passes through the various materials between the analyte and the objective lens 144.

Figure 19:
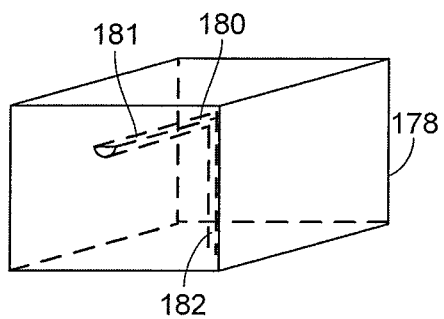
FIG. 19 is a perspective view of a body for use in a flow cytometer according to the described methods and apparatus.
Figure 20:
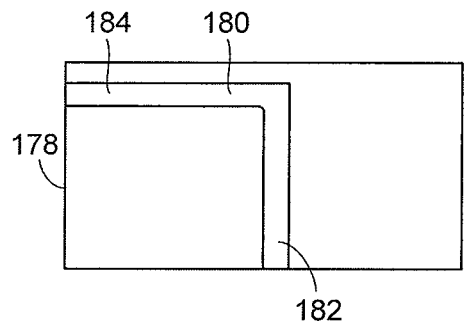
FIG. 20 is a cross-sectional view of the body of FIG. 19.

FIGS. 19 and 20 illustrate a perspective view and a cross-sectional view, respectively, of a body 178 in which a flow path 180 may be formed. The flow path 180 creates an inverted "L" shape within the body 178. The flow path 180 has an entrance flow section 182 and an exit flow section 184. While the figures illustrate the entrance flow section 182 as a right circular cylinder and the exit flow section 184 as a channel, the respective sections 182 and 184 may have any desired cross-sectional shape. In accordance with the methods and apparatus described, the body 178 may be formed of a material having a refractive index similar to or the same as either or both of a fluid (not shown) flowing through the flow path 180, or a fluid (not shown) in which an objective lens (not shown) is immersed or dipped. In this manner, the embodiments depicted in FIGS. 19 and 20 mitigate or eliminate the effects of refraction as light passes through the various materials between the analyte and the objective lens.

Figure 21:
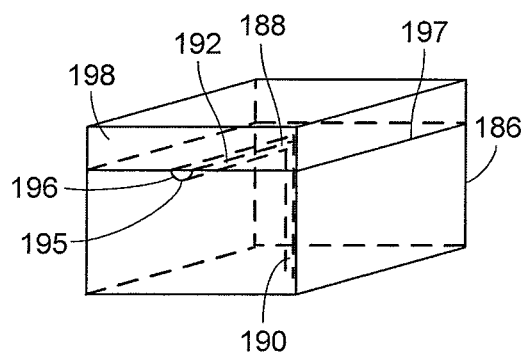
FIG. 21 is a perspective view of a body and transparent boundary material for use in a flow cytometer according to the described methods and apparatus.
Figure 22:
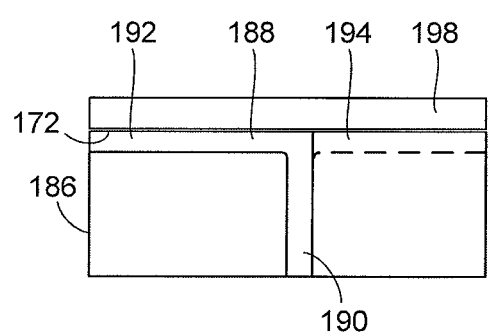
FIG. 22 is a cross-sectional view of the body of FIG. 21.

FIGS. 21 and 22 depict a perspective view and a cross-sectional view, respectively, of a body 186 in which a flow path 188 may be formed. The flow path 188 includes an entrance flow section 190 and an exit flow section 192, and may optionally include a transverse flow entrance section 194 (shown as a broken line). In contrast to the embodiment depicted in FIGS. 19 and 20, the exit flow section 192 (and the transverse flow entrance section 194) may be formed as a channel 195 having edges 196 that are generally coplanar with a top surface 197 of the body 186. An optional transparent boundary material 198 may be disposed between the body 186 and an objective lens (not shown). In accordance with the methods and apparatus described, the body 186 and/or the transparent boundary material 198 may be formed of a material having a refractive index similar to or the same as either or both of a fluid (not shown) flowing through the flow path 188, or a fluid (not shown) in which the objective lens is immersed or dipped. In this manner, the embodiments depicted in FIGS. 21 and 22 mitigate or eliminate the effects of refraction as light passes through the various materials between the analyte and the objective lens.

Figure 23:
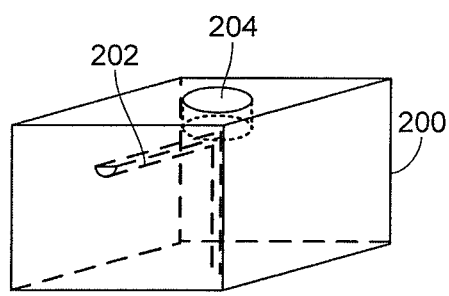
FIG. 23 is a perspective view of a body for use in a flow cytometer, the body having a window, insert, or opening in accordance with the described methods and apparatus.
Figure 24:
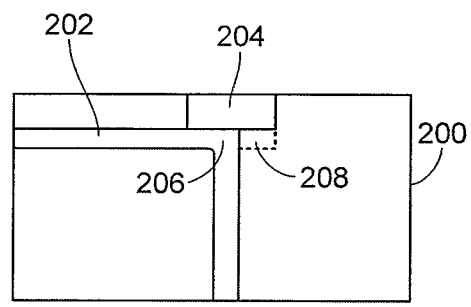
FIG. 24 is a cross-sectional view of the body of FIG. 23.

FIGS. 23 and 24 illustrate a perspective view and a cross-sectional view, respectively, of an embodiment according the methods and apparatus described, in which a flow path 202 is formed in a body 200. The flow path 202, while illustrated as forming an inverted "L" shape, may also form a "T" shape as depicted in FIGS. 15-18. In the embodiment illustrated in FIGS. 23 and 24, the body 200 may or may not be formed of a material having a refractive index similar to or the same as either or both of a fluid (not shown) flowing through the flow path 202, or a fluid (not shown) in which an objective lens (not shown) is immersed or dipped. An insert, window, or opening 204 allows the objective lens to view a section 206 of the flow path 202. The insert, window, or opening 204 may be a negative space, open to the flow path 202, may be a window covering a negative space over the flow path 202, or may be an insert disposed within the body such that a surface of the insert is in contact with the flow path 202 and/or a fluid (not shown) in the flow path 202. Further, where the body includes the insert 204, the insert 204 may extend into an area 208 (shown as a broken line) along one side of the flow path 202. While the insert, window, or opening 204 is depicted in FIGS. 23 and 24 as circular, the insert, window, or opening 204 may be any desired shape. In accordance with the methods and apparatus described, where the body 200 includes the insert or window 204, the insert or window 204 may be formed of a material having a refractive index similar to or the same as either or both of the fluid flowing through the flow path 202, or the fluid in which the objective lens is immersed or dipped. In this manner, the embodiments depicted in FIGS. 23 and 24 mitigate or eliminate the effects of refraction as light passes through the various materials between the analyte and the objective lens.

Figure 25:
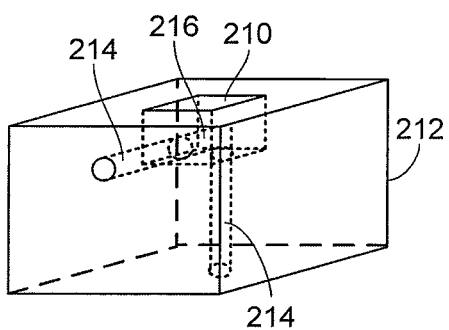
FIG. 25 is a perspective view of a body for use in a flow cytometer, the body having an insert in accordance with the described methods and apparatus.
Figure 26:
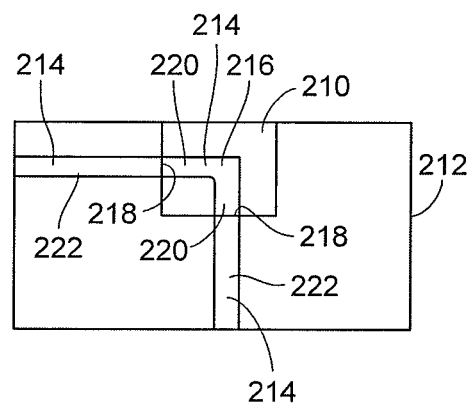
FIG. 26 is a cross-sectional view of the body of FIG. 25.

In some embodiments, illustrated in FIGS. 25 and 26 in perspective and cross-sectional views, respectively, a body 210, such as the bodies 174, 178, 186, and 200, formed at least in part by a material having a refractive index similar to or the same as either or both of the fluid flowing through the flow path or the fluid in which the objective lens is immersed or dipped, may be inset into a larger body 212 in which a flow path 214 is formed. A portion 216 of the flow path 214 passes through the body 210. Openings 218 at the ends 220 of the portion 216 align with portions 222 of the flow path 214 in the larger body 212. While FIGS. 25 and 26 depict the body 210 as a rectangular cuboid, the body 210 may be any desired shape and, in particular, may be cylindrical.

Figure 27:
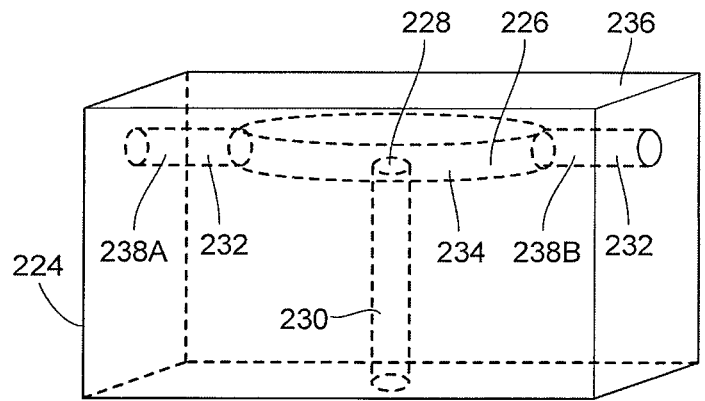
FIG. 27 is a perspective view of an alternate embodiment of a body for use in a flow cytometer in accordance with the described methods and apparatus.

In still other embodiments, such as that depicted in FIG. 27, a body 224 includes a reservoir 226 formed at an intersection 228 of a first flow path portion 230 and a second flow path portion 232. For example, the first flow path portion 230 may intersect the reservoir 226 at a generally planar bottom surface 234 that is generally parallel to a surface 236 of the body 224. Two parts 238A and 238B of the second flow path portion 232 may connect to the reservoir 226 at opposing surfaces of the reservoir 226, which may generally have the shape of a flattened cylinder. Of course, the reservoir 226 could be any desirable shape including, by way of example, a flattened cuboid. Further, there is no requirement that the second flow path portion 232 include both the parts 238A and 238B. That is, the flow path 232 need not include a transverse flow but, instead, could include only the outlet portion 238A. In accordance with the methods and apparatus described, the body 224 may be formed of a material having a refractive index similar to or the same as either or both of a fluid (not shown) flowing through the flow path portions 230 and 232 and the reservoir 226, or a fluid (not shown) in which the objective lens (not shown) is immersed or dipped. In this manner, the embodiments depicted in FIG. 27 mitigate or eliminate the effects of refraction as light passes through the various materials between the analyte and the objective lens.

Figure 28:
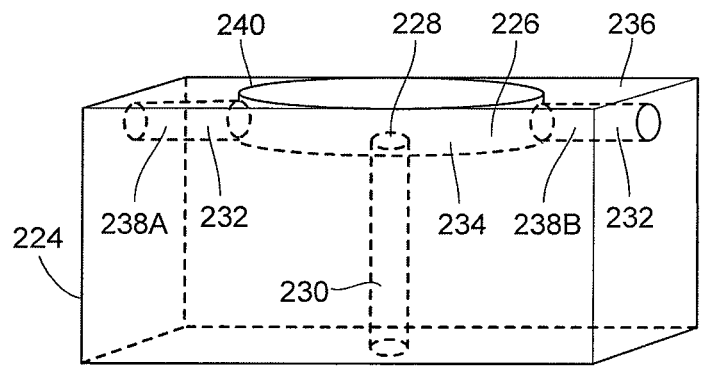
FIG. 28 is a perspective view of alternate embodiment of the body depicted in FIG. 27.

FIG. 28 depicts a related embodiment in which a top edge 240 of the reservoir 226 is coplanar with the surface 236 of the body 224. A water-dipping objective lens (not shown) may extend into the reservoir 226 and, in doing so, may be in contact with fluid flowing through the flow paths 230 and 232 and the reservoir 226, which may mitigate and/or eliminate any interfaces between materials of differing refractive indices.

Figure 29:
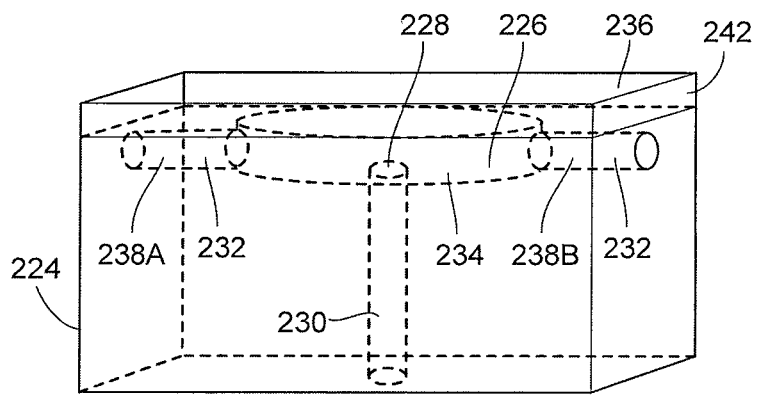
FIG. 29 is a perspective view of another alternate embodiment of the body depicted in FIG. 27 with an associated transparent boundary material.

FIG. 29 depicts yet another related embodiment, in which a transparent boundary material 242 is placed over the exposed reservoir 226 depicted in the embodiment of FIG. 28.

Figure 30:
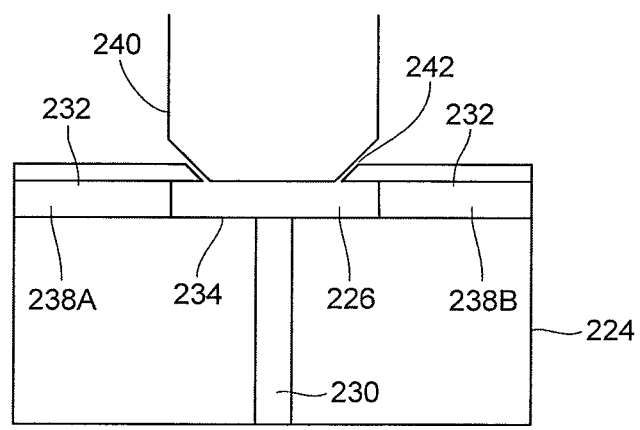
FIG. 30 is a cross-sectional view of yet another alternate embodiment of the body depicted in FIG. 28, in which an objective lens functions as a wall of the flow path.

FIG. 30 depicts still another related embodiment, in which an objective lens 240 (which may be a water dipping objective lens) protrudes through an opening 242 into the body 224 to form a boundary of the flow path 232 and, in particular, to form a boundary of the reservoir 226.

Each of the bodies 174, 178, 186, 200, 212, and 234 may be formed from one of a perfluoroalkoxy polymer, an amorphous fluoropolymer, or an amorphous perfluoropolymer, particularly in applications in which the analyte is suspended in, carried in, or bathed by a medium having a refractive index close to that of water. Further, each of the bodies 174, 178, 186, 200, and 234 may be integral to a flow cytometer in accordance with the described methods and apparatus, or may be a separable (i.e., removable, replaceable, etc.) component of the flow cytometer. In some embodiments, one of the bodies 174, 178, 186, 200, and 234 may be part of a cartridge, installed in the flow cytometer according to the application or according to the analyte. In some embodiments the cartridge may be reusable and/or amenable to sterilization. The bodies 174, 178, 186, 200, and 234 and, in particular, respective flow paths therein, need not comprise the entire flow path of the flow cytometer and, accordingly, may connect to other flow path portions in the flow cytometer.

Although the foregoing text sets forth a detailed description of numerous different embodiments, it should be understood that the scope of protection is defined by the words of the claims to follow. The detailed description is to be construed as exemplary only and does not describe every possible embodiment because describing every possible embodiment would be impractical, if not impossible. One could implement numerous alternative embodiments using either current technology or technology developed after the filing date of this patent, which embodiments would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims. The specification above describes at least the following aspects:

1. A flow cytometer comprising:
a flow path having an input, an output, and a detection region;
an excitation energy source;
a detector;
a processor communicatively coupled to the detector and to a memory device;
an optical focusing element having a focal point in the detection region, the boundaries of the optical focusing element cooperating with the focal point to define a virtual conical volume;
wherein a component of the flow cytometer disposed at least partially within the virtual conical volume, or disposed at least partially within a volume through which light from the focal point passes between the focal point and the optical focusing element, comprises a material having a refractive index between 1.30 and 1.40 inclusive.

2. The flow cytometer of aspect 1, wherein the component comprises one or more of the group consisting of: a perfluoroalkoxy polymer; an amorphous fluoropolymer; and an amorphous perfluoropolymer.

3. The flow cytometer of aspect 1 or aspect 2, wherein the optical focusing element is an objective lens.

4. The flow cytometer of aspect 3, wherein the objective lens is a corrected objective lens.

5. The flow cytometer of aspect 4, wherein the objective lens is either a water-dipping objective lens or a water-immersion objective lens.

6. A cytometer comprising a volume defined by an objective lens and a focal point associated with the objective lens, the volume including a material having a refractive index between 1.30 and 1.40 inclusive.

7. The cytometer of aspect 6, wherein the material forms at least a portion of one or more of the group consisting of: an optical cell; a window; a cuvette; a tube; a passage; a chamber; a slide; a wall; and a boundary.

8. The cytometer of aspect 6 or aspect 7, wherein the material comprises one of the group consisting of: a perfluoroalkoxy polymer; an amorphous fluoropolymer; and an amorphous perfluoropolymer.

9. The cytometer of any of aspects 6 to 8, wherein the cytometer is a flow cytometer.

10. The cytometer of aspect 9, further comprising a flow path having a curvilinear cross-section.

11. The cytometer of any of aspects 6 to 10, further comprising either a water immersion objective lens or a water dipping objective lens.

12. The cytometer of aspect 11, wherein the objective lens is in contact with one of the group consisting of: a buffer solution; a sheath fluid; a growth medium; and a fluid used to carry, suspend, or bathe the analyte.

13. The cytometer of aspect 11, wherein the objective lens is in direct contact with the material having a refractive index between 1.30 and 1.40 inclusive.

14. The cytometer of aspect 13, wherein the material having a refractive index between 1.30 and 1.40 inclusive, is also in contact with one of the group consisting of: a buffer solution; a sheath fluid; a growth medium; and a fluid used to carry, suspend, or bathe the analyte.

15. A method of performing cytometry of an analyte, the method comprising adjusting the refractive index of a first material such that the difference between the refractive index of the first material and the refractive index of a second material is less than 0.02.

16. The method of aspect 15, wherein the first material is used to carry the analyte, suspend the analyte, or bathe the analyte.

17. The method of aspect 15, wherein the first material is one of the group consisting of: a buffer solution; a sample fluid; a sheath fluid; a growth medium; and a lens immersion fluid.

18. The method of any of aspects 15 to 17, wherein the second material is one of the group consisting of: an optical cell; a window; a cuvette; a tube; a passage; a chamber; a slide; a wall; and a boundary.

19. The method of any of aspects 15 to 18, wherein the second material has a refractive index between 1.30 and 1.40 inclusive.

20. The method of any of aspects 15 to 19, wherein the second material comprises one or more of the group consisting of: a perfluoroalkoxy polymer; an amorphous fluoropolymer; and an amorphous perfluoropolymer.

I claim:

1. A flow cytometer comprising:
a flow path having an input, an output, and a detection region;
an excitation energy source;
a detector;
a processor communicatively coupled to the detector and to a memory device;
a sorting mechanism; and
an optical focusing element having a focal point in the detection region, the boundaries of the optical focusing element cooperating with the focal point to define a virtual conical volume;
wherein the axis of the virtual conical volume is coaxial with respect to the flow axis of the flow path;
wherein a component of the flow cytometer disposed at least partially within the virtual conical volume, or disposed at least partially within a volume through which light from the focal point passes between the focal point and the optical focusing element, comprises a material having a refractive index between 1.30 and 1.40 inclusive.

2. The flow cytometer of claim 1, wherein the component comprises one or more of the group consisting of: a perfluoroalkoxy polymer; an amorphous fluoropolymer; and an amorphous perfluoropolymer.

3. The flow cytometer of claim 1, wherein the optical focusing element is an objective lens.

4. The flow cytometer of claim 3, wherein the objective lens is a corrected objective lens.

5. The flow cytometer of claim 4, wherein the objective lens is either a water-dipping objective lens or a water-immersion objective lens.

6. A cytometer comprising a conical volume defined by (1) an objective lens focusing for a detector radiation from particles in a flow path and (2) a focal point associated with the objective lens, the volume having an axis coaxial with respect to a flow axis of the flow path passing through the focal point, and including a solid material having a refractive index between 1.30 and 1.40 inclusive, wherein the cytometer is a sorting flow cytometer.

7. The cytometer of claim 6, wherein the solid material forms at least a portion of one or more of the group consisting of: an optical cell; a window; a cuvette; a tube; a passage; a chamber; a slide; a wall; and a boundary.

8. The cytometer of claim 6, wherein the solid material comprises one of the group consisting of: a perfluoroalkoxy polymer; an amorphous fluoropolymer; and an amorphous perfluoropolymer.

9. The cytometer of claim 6, further comprising a flow path having a curvilinear cross-section.

10. The cytometer of claim 6, further comprising either a water immersion objective lens or a water dipping objective lens.

11. The cytometer of claim 10, wherein the objective lens is in contact with one of the group consisting of: a buffer solution; a sheath fluid; a growth medium; and a fluid used to carry, suspend, or bathe the analyte.

12. The cytometer of claim 10, wherein the objective lens is in direct contact with the solid material having a refractive index between 1.30 and 1.40 inclusive.

13. The cytometer of claim 12, wherein the solid material having a refractive index between 1.30 and 1.40 inclusive, is also in contact with one of the group consisting of: a buffer solution; a sheath fluid; a growth medium; and a fluid used to carry, suspend, or bathe the analyte.

14. A method of performing cytometry of an analyte, the method comprising adjusting the refractive index of a first material such that the difference between the refractive index of the first material and the refractive index of a second, solid material is less than 0.02, wherein performing cytometery comprises performing flow cytometry and wherein the second material comprises one or more of the group consisting of: a perfluoroalkoxy polymer; an amorphous fluoropolymer; and an amorphous perfluoropolymer.

15. The method of claim 14, wherein the first material is used to carry the analyte, suspend the analyte, or bathe the analyte.

16. The method of claim 14, wherein the first material is one of the group consisting of: a buffer solution; a sample fluid; a sheath fluid; a growth medium; and a lens immersion fluid.

17. The method of claim 14, wherein the second material is one of the group consisting of: an optical cell; a window; a cuvette; a tube; a passage; a chamber; a slide; a wall; and a boundary.

18. The method of claim 14, wherein the second material has a refractive index between 1.30 and 1.40 inclusive.

19. A cytometer comprising a conical volume defined in part by focal point associated with an optical element, the volume including a material having a refractive index between 1.30 and 1.40 inclusive, wherein the cytometer is a sorting flow cytometer, wherein the axis of the volume is coaxial with respect to a flow axis passing through the focal point, and wherein the material comprises one of the group consisting of: a perfluoroalkoxy polymer; an amorphous fluoropolymer; and an amorphous perfluoropolymer.

20. The cytometer of claim 19, wherein the material forms at least a portion of one or more of the group consisting of: an optical cell; a window; a cuvette; a tube; a passage; a chamber; a slide; a wall; and a boundary.

21. The cytometer of claim 19, further comprising either a water immersion objective lens or a water dipping objective lens.

22. The cytometer of claim 21, wherein the objective lens is in contact with one of the group consisting of: a buffer solution; a sheath fluid; a growth medium; and a fluid used to carry, suspend, or bathe the analyte.

23. The cytometer of claim 21, wherein the objective lens is in direct contact with the material having a refractive index between 1.30 and 1.40 inclusive.

24. The cytometer of claim 23, wherein the material having a refractive index between 1.30 and 1.40 inclusive, is also in contact with one of the group consisting of: a buffer solution; a sheath fluid; a growth medium; and a fluid used to carry, suspend, or bathe the analyte.

25. A cytometer comprising:
a volume defined by an objective lens and a focal point associated with the objective lens, the volume including a material having a refractive index between 1.30 and 1.40 inclusive; and
a water immersion objective lens or a water dipping objective lens;
wherein the cytometer is a flow cytometer, and
wherein the objective lens is in contact with one of the group consisting of: a buffer solution; a sheath fluid; a growth medium; and a fluid used to carry, suspend, or bathe the analyte.

26. The cytometer of claim 25, wherein the material forms at least a portion of one or more of the group consisting of: an optical cell; a window; a cuvette; a tube; a passage; a chamber; a slide; a wall; and a boundary.

27. The cytometer of claim 25, wherein the objective lens is in direct contact with the material having a refractive index between 1.30 and 1.40 inclusive.

28. The cytometer of claim 27, wherein the material having a refractive index between 1.30 and 1.40 inclusive, is also in contact with one of the group consisting of: a buffer solution; a sheath fluid; a growth medium; and a fluid used to carry, suspend, or bathe the analyte.

* * * * *

UNITED STATES PATENT AND TRADEMARK OFFICE
CERTIFICATE OF CORRECTION

| | | |
|---|---|---|
| PATENT NO. | : 8,665,439 B2 | Page 1 of 1 |
| APPLICATION NO. | : 12/495437 | |
| DATED | : March 4, 2014 | |
| INVENTOR(S) | : Mark Luscher | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this
Twelfth Day of May, 2015

Michelle K. Lee
*Director of the United States Patent and Trademark Office*